US006180404B1

(12) United States Patent
Brewer et al.

(10) Patent No.: US 6,180,404 B1
(45) Date of Patent: Jan. 30, 2001

(54) CULTURAL MEDIUM FOR MAINTAINING NEURAL CELLS IN AMBIENT ATMOSPHERE

(75) Inventors: Gregory J. Brewer, Springfield, IL (US); Paul J. Price, Grand Island, NY (US)

(73) Assignee: The Board of Trustees of Southern Illinois University, Springfield, IL (US)

( * ) Notice: Under 35 U.S.C. 154(b), the term of this patent shall be extended for 0 days.

(21) Appl. No.: 09/155,803

(22) PCT Filed: Apr. 9, 1997

(86) PCT No.: PCT/US97/05875

§ 371 Date: Jun. 14, 1999

§ 102(e) Date: Jun. 14, 1999

(87) PCT Pub. No.: WO97/38090

PCT Pub. Date: Oct. 16, 1997

Related U.S. Application Data
(60) Provisional application No. 60/015,049, filed on Apr. 9, 1996.

(51) Int. Cl.⁷ .............................. C12N 5/02; C12N 5/06; C12N 5/08
(52) U.S. Cl. .................. 435/405; 435/325; 435/366; 435/368; 435/374; 435/404; 435/406; 424/93.7
(58) Field of Search ...................... 435/325, 366, 435/368, 404, 405, 406, 374; 424/93.7

(56) References Cited

U.S. PATENT DOCUMENTS

| | | |
|---|---|---|
| 4,798,824 | 1/1989 | Belzer et al. . |
| 4,873,230 | 10/1989 | Belzer et al. . |
| 4,879,283 | 11/1989 | Belzer et al. . |
| 5,316,938 * | 5/1994 | Keen et al. ........................ 435/404 |
| 5,716,847 * | 2/1998 | Simmons et al. .................. 435/404 |

OTHER PUBLICATIONS

G.J. Brewer, Serum–Free B27/Neurobasal Medium Supports Differentiated Growth of Neurons From the Striatum, Substantia Nigra, Septum, Cerebral Cortex, Cerebellum, and Dentate Gyrus, Journal of Neuroscience Research 42;674–683 (1995).

G.T. Spierenburg, G.T.J.J. Oerlemans, J.P.R.M. Van Laarhoven, and C.H.M.M. De Bruyn, Phototoxicity of N–2–Hydroxyethylpiperazine–N'–2–ethanesulfonic Acid–buffered Culture Media for Human Leukemic Cell Lines, Cancer Research, May 1984, 44, 2253–2254.

Jerrolynn C. Kawamoto and John N. Barrett, Cryopreservation of Primary Neurons for Tissue Culture, Brain Research, 1986, 384 (1986) 84–93.

Albert Leibovitz, The Growth And Maintenance Of Tissue–Cell Cultures In Free Gas Exchange With The Atmosphere, Am.J.Hyg. 1963, vol. 78; 173–180.

C. Ward Kischer, A. Leibovitz and J. Pindur, The use of a transport medium (L15M15) for bulk tissue storage and retention of viability, Cytotechnology, 2: 181–185, 1989.

Product Catalogue and Reference Guide 1995–1996, Life Technologies, Producer of Gibco BRL Products.

Brewer et al. NeuroReport. vol. 7, No. 9, pp. 1509–15–12, Jun. 1996.*

Brewer et al. J. Neurosci. Res. vol. 35, pp. 567–576, 1993.*

Church et al. J. Physiol. vol. 455, pp. 51–71, 1992.*

Eckerman et al. Am. J. Physiol. vol. 258 (5 Part 2), pp. R1140–R1146, 1990.*

Braschler et al. J. Neurosci. Methods, vol. 29, pp. 121–129, 1989.*

Matsumura et al. Pflueglers Arch. Eur. J. Physiol. vol. 2, pp. 120–123, abstract enclosed, 1987.*

Dean et al. Neurosci. vol. 36 (1), pp. 207–216, abstract enclosed, 1990.*

Walter, I. Devel. Biol. vol. 161 (1), pp. 263–273, abstract enclosed, 1994.*

* cited by examiner

*Primary Examiner*—Christopher Tate
(74) *Attorney, Agent, or Firm*—Rockey, Milnamow & Katz, Ltd.

(57) ABSTRACT

The present invention provides a minimal essential medium for maintaining neural cell or tissue viability in an environment containing ambient levels of $CO_2$. The medium contains less than about 2000 $\mu$M bicarbonate, a buffer having a pKa of from about 6.9 to about 7.7, wherein the medium is free of ferrous sulfate, glutamate and aspartate, from 0 to about 3000 $\mu$M $CaCl_2$, from about 0.05 to about 0.8 $\mu$M $Fe(NO_3)_3$, from about 2500 to about 10000 $\mu$M KCl, from 0 to about 4000 $\mu$M $MgCl_2$, from about 74000 to about 103000 $\mu$M NaCl, from about 400 to about 2000 $\mu$M $NaHCO_3$, from about 250 to about 4000 $\mu$M $NaH_2PO_4$, from about 0.2 to about 2 $\mu$M $ZnSO_4$, from about 2500 to about 50000 $\mu$M glucose and from about 23 to about 500 $\mu$M sodium pyruvate. The present invention also provides a process of extending neural cell or tissue viability in an atmosphere having ambient levels of carbon dioxide whereby the neural cells or tissue are placed in such a medium. Preferably, the medium is supplemented with a growth-promoting medium that contains effective amounts of hormones, essential fatty acids and anti-oxidants for neural cells.

24 Claims, 2 Drawing Sheets

CULTURAL MEDIUM FOR MAINTAINING NEURAL CELLS IN AMBIENT ATMOSPHERE

This application is a 371 of PCT/US97/05875, filed Apr. 9, 1997, which claims priority to U.S. Provisional application Serial No. 60/015,049, filed Apr. 9, 1996.

TECHNICAL FIELD OF THE INVENTION

The field of this invention is cell culture media. More particularly, the present invention pertains to a medium for neural cells or tissue that maintains viability of those cells or tissue in an atmosphere having ambient levels of carbon dioxide.

BACKGROUND OF THE INVENTION

A major problem attendant to studies of central nervous system tissue is the maintenance of cell viability of such tissues. The inability to maintain central nervous system tissue viability in culture for prolonged periods of time and under various environmental conditions has impeded the development of effective therapeutic regimens for treating central nervous system disorders.

A nutrient balanced salt solution (medium) for maintaining central nervous system tissue viability in a high-carbon dioxide atmosphere (5% $CO_2$) has recently been developed. That medium, Neurobasal™ (Gibco/Life Technologies, Inc., Gaithersburg, Md.), is a bicarbonate buffered medium optimized for the growth of embryonic rat hippocampal neurons at a pH of 7.3 in 5% $CO_2$. Neurobasal™ is a derivative of Dulbecco's Modified Eagle's Medium (DMEM) and was formulated to optimize embryonic rat hippocampal cell survival. When compared to DMEM, Neurobasal™ has less NaCl and less $NaHCO_3$, resulting in a lower osmolality, and lesser amounts of cysteine and glutamine, resulting in diminished glial growth. In addition, Neurobasal™ contains alanine, asparagine, proline and vitamin B12, all of which are absent from DMEM.

Although neurons can be maintained in a 5% $CO_2$ atmosphere in this high bicarbonate medium, when supplemented with B27 (a hormone and anti-oxidant supplement available from Life Technologies, Inc.), neurons undergo rapid death when transferred to ambient $CO_2$ (0.2%) conditions. Death is associated with a rapid rise in medium pH to a value of 8.1.

The preparation and study of neural tissue and cells frequently requires the use of ambient $CO_2$ levels outside of an incubator. Existing methods for controlling the pH of cells outside of incubators include the use of weak buffers (e.g., as found in Dulbecco's modified Eagle's medium or L 15 medium) and the use of continuous gassing with 5–10% $CO_2$ to maintain physiological pH.

A simple test, however, shows that ambient $CO_2$ causes the pH of DMEM to quickly rise to a value of 8.1 outside the incubator. The common practice of buffering with HEPES slows but does not prevent this substantial alkalinization. The practice of continuously gassing tissues to maintain high $CO_2$ levels and physiological pH is cumbersome and expensive. There continues to be a need in the art, therefore, for a medium that can maintain physiological pH and neural cell viability in ambient $CO_2$ conditions.

BRIEF SUMMARY OF THE INVENTION

In one aspect, the present invention provides a minimal essential medium for maintaining neural cell or tissue viability in an environment containing ambient levels of $CO_2$. The medium contains less than about 2000 μM bicarbonate, has an osmolality of from about 230 mOsm to about 300 mOsm, contains a buffer having a pKa of from about 6.9 to about 7.7, and is free of ferrous sulfate, glutamate and aspartate. A medium of the present invention is effective in maintaining viability of neural cells or tissue derived from embryonic tissues or adult tissues.

Where the cells or tissue are of embryonic origin, the osmolality is from about 230 mOsm to about 250 mOsm. Such a medium comprises, in final concentration, 0 to about 3000 μM $CaCl_2$, 0.05 to about 0.8 μM $Fe(NO_3)_3$, 2500 to about 10000 μM KCl, 0 to about 4000 μM $MgCl_2$, 74000 to about 81000 μM NaCl, 400 to about 2000 μM $NaHCO_3$, 250 to about 4000 μM $NaH_2PO_4$, 0.2 to about 2 μM $ZnSO_4$, 2500 to about 5000 μM glucose, 0 to about 100 μM phenol red, and 23 to about 500 μM sodium pyruvate.

Where the neural cells or tissue are of adult origin, the osmolality is from about 250 mOsm to about 300 mOsm. Such a medium comprises, in final concentration, 0 to about 3000 μM $CaCl_2$, 0.05 to about 0.8 μM $Fe(NO_3)_3$, 2500 to about 10000 μM KCl, 0 to about 4000 μM $MgCl_2$, 86000 to about 103000 μM NaCl, 400 to about 2000 μM $NaHCO_3$, 250 to about 4000 μM $NaH_2PO_4$, 0.2 to about 2 μM $ZnSO_4$, 2500 to about 5000 μM glucose, 0 to about 100 μM phenol red, and 23 to about 500 μM sodium pyruvate.

A preferred buffer is 3-[N-morpholino]propane-sulfonic acid (MOPS). A medium of the present invention contains effective amounts of at least ten essential amino acids. In one embodiment, the medium contains, in final concentration: a) from about 250 to about 2500 μM each of L-isoleuoine, L-leucine, L-threonine and L-valine; b) from about 150 to about 1500 μM L-glutamine; c) from about 120 to about 1200 μM each of L-arginine, glycine, L-phenylalanine, L-serine and L-tyrosine; d) from about 60 to about 600 μM each of L-histidine and L-methionine; e) from about 25 to about 250 μM L-tryptophan; f) from about 25 to about 250 μM L-proline; g) from about 6 to about 60 μM L-alanine; h) from about 3 to about 30 μM L-cysteine; and i) from about 1.5 to about 15 μM each of L-asparagine and L-lysine.

A medium of the present invention further includes vitamins in amounts effective to sustain neural cell or tissue viability. The medium contains, in final concentration, from about 12 to about 120 μM i-inositol, from about 10 to about 100 μM niacinamide, from about 9 to about 90 μM choline chloride, from about 6 to about 60 μM pyridoxal, from about 3 to about 30 μM thiamine, from about 2.5 to about 25 μM each of folic acid and D-Ca pantothenate, from about 0.3 to about 3 μM riboflavin, and from about 0.06 to about 0.6 μM vitamin B12.

In another aspect, the present invention provides a process of extending neural cell or tissue viability in an atmosphere having ambient levels of carbon dioxide. The process includes the steps of placing neural cells or tissue in a medium of the present invention and maintaining the cells or tissue in that medium under ambient $CO_2$ conditions. In a preferred embodiment of a process of the present invention, the medium is supplemented with a serum-free growth promoting supplement that contains effective amounts of hormones, essential fatty acids and anti-oxidants for neural cells. A preferred growth-promoting supplement contains biotin, L-carnitine, corticosterone, ethanolamine, D(+)-galactose, reduced glutathione, linoleic acid, linolenic acid, progesterone, putrescine, retinyl acetate, selenium, triodo-1-thyronine, DL-α tocopherol, DL-α tocopherol acetate, bovine albumin, catalase, insulin, superoxide dismutase and transferrin.

The present invention also provides a composition comprising neural cells or tissue in a medium as set forth above. The medium containing the cells or tissue can optionally be supplemented with a growth-promoting supplement as described above.

BRIEF DESCRIPTION OF THE DRAWINGS

In the drawings, which form a portion of the specification.

DETAILED DESCRIPTION OF THE INVENTION

I. Composition of Matter

Figure 1:
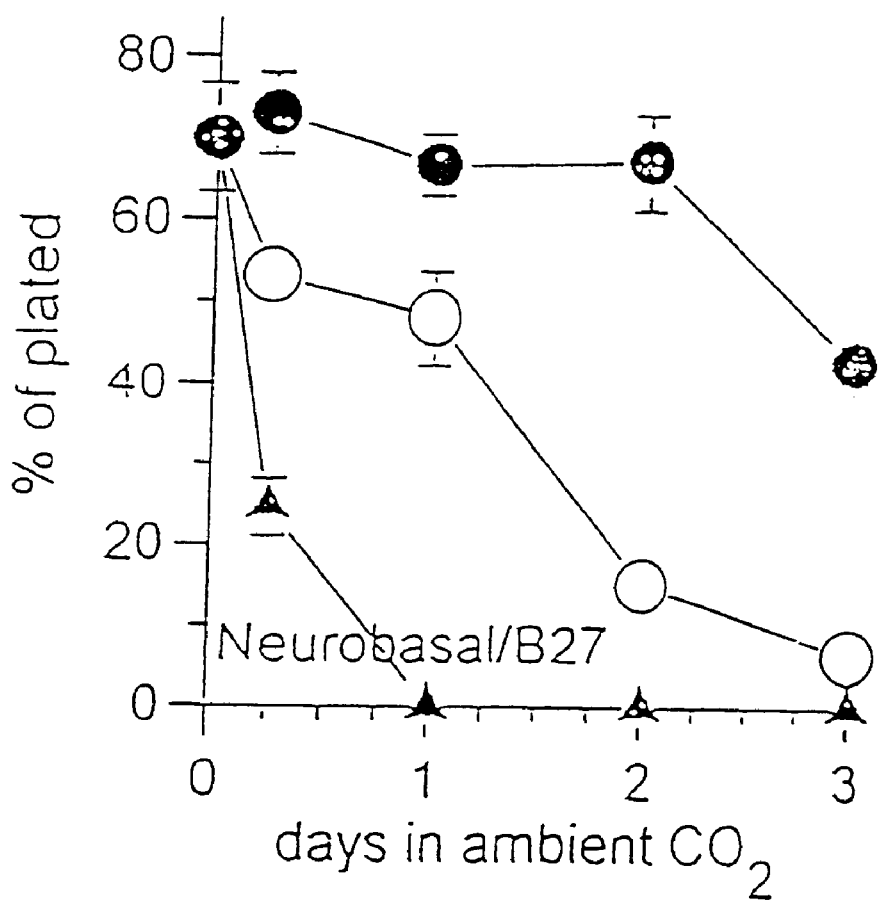
FIG. 1 shows the viability of neurons cultured for four days in B27-supplemented Neurobasal™ in 5% $CO_2$ and then transferred to a medium of the present invention either alone (-○-) or supplemented with B27(-●-).

In one aspect, the present invention provides a medium for neural cells or tissue maintained in an environment containing ambient amounts of carbon dioxide ($CO_2$). As is well known in the art, ambient air contains less than about 0.25% $CO_2$ and, more typically, about 0.2% $CO_2$. A medium of the present invention is designed and formulated to allow for prolonged survival and viability of neural cells or tissue exposed to such low $CO_2$ levels.

As is well known in the art, there are a variety of preparative steps to obtain primary neural cell cultures. By way of example, specific regions of the brain are typically dissected as a tissue and placed in a suitable medium. This neural tissue is further processed to obtain cells which are typically plated in a culture container and the medium is placed over the plated tissue. In both cases, the medium is changed as needed to maintain viability. As used herein, the terms "suspended" or "cultured" are used to refer both to suspensions of tissue, or individual cells and plated individual cells. As used herein, the phrase "neural cells" means either individual cells of the same or different type whether those cells exist as isolated cells or exist in the form of aggregates or collections.

A medium of the present invention is a derivative of a basal medium previously described by the present inventor to provide prolonged viability of neural cells or tissue in a high-$CO_2$ environment (e.g., 5% $CO_2$) such as typically used in cell incubators (Brewer et al., J. Neuroscience Res., 35:567–576, 1993). The basal medium described in that publication was designated Neurobasal™.

A medium of the present invention contains the same nutrients (e.g., glucose, amino acids) and vitamins as Neurobasal™. Differences between Neurobasal™ and a medium of the present invention are changes in the levels of bicarbonate and sodium chloride and the use of MOPS as the inert buffer (HEPES is used in Neurobasal™).

Like Neurobasal™, a medium of the present invention can be used with neural cells or tissue derived from any area of the central nervous system of a mammal, including humans. The cells or tissues can be derived or obtained from embryonic, neo-natal or adult central nervous system tissue. A medium of the present invention can also be used to maintain viability of neural cells or tissue obtained after death of the donor animal (post-mortem harvesting). Post-mortem tissue harvesting is particularly important where the donor animal is killed rather than anesthetized prior to tissue extraction.

A medium of the present invention is characterized by the presence of very low levels of a bicarbonate buffer system. The pH value of the medium is controlled predominantly by non-bicarbonate buffers. Those buffers include sodium phosphate (e.g., $NaH_2PO_4$) and inert buffers having a pKa between a pH value of about 6.9 and about 7.7. Such inert buffers are well known to those of skill in the art and readily available from commercial sources. A preferred such inert buffer is 3-[N-morpholino] propane-sulfonic acid (MOPS) having a pKa of about 7.2. An inert buffer used in a medium of the present invention must be non-toxic toward neural cells. Thus, for example, the use of HEPES, which has been shown to be phototoxic to certain neural cells should be avoided. The inert buffer is present at a final concentration of from about 5000 μM to about 25000 μM and, more preferably from, about 8000 μM to about 12000 μM.

A medium of the present invention is effective in maintaining viability of neural cells or tissue derived from embryonic tissues or adult tissues. Where the cells or tissue are of embryonic origin, the medium has an osmolality from about 230 mOsm to about 250 mOsm. Such a medium comprises, in final concentration, from 0 to about 3000 μM $CaCl_2$, from about 0.05 to about 0.8 μM $Fe(NO_3)_3$, from about 2500 to about 10000 μM KCl, from 0 to about 4000 μM $MgCl_2$, from about 74000 to about 81000 μM NaCl, from about 400 to about 2000 μM $NaHCO_3$, from about 250 to about 4000 μM $NaH_2PO_4$, from about 0.2 to about 2 μM $ZnSO_4$, from about 2500 to about 50000 μM glucose, from 0 to about 100 μM phenol red, and from about 23 to about 500 μM sodium pyruvate. More preferably, such a medium comprises, in final concentration, from about 900 to about 2500 μM $CaCl_2$, from about 0.1 to about 0.4 μM $Fe(NO_3)_3$, from about 4000 to about 7000 μM KCl, from 500 to about 1500 μM $MgCl_2$, from about 75000 to about 77000 μM NaCl, from about 600 to about 1200 μM $NaHCO_3$, from about 600 to about 1200 μM $NaH_2PO_4$, from about 0.4 to about 1.2 μM $ZnSO_4$, from about 15000 to about 35000 μM glucose, from about 15 to about 40 μM phenol red, and from about 150 to about 250 μM sodium pyruvate.

An especially preferred such medium comprises, in final concentration, 1800 μM $CaCl_2$, 0.2 μM $Fe(NO_3)_3$, 5360 μM KCl, 812 μM $MgCl_2$, 76000 μM NaCl, 880 μM $NaHCO_3$, 900 μM $NaH_2PO_4$, 0.67 μM $ZnSO_4$, 25000 μM glucose, 23 μM phenol red, and 230 μM sodium pyruvate.

Where the neural cells or tissue are of adult origin, the osmolality is is from about 250 mOsm to about 300 mOsm. Such a medium comprises, in final concentration, from 0 to about 3000 μM $CaCl_2$, from about 0.05 to about 0.8 μM $Fe(NO_3)_3$, from about 2500 to about 10000 μM KCl, from 0 to about 4000 μM $MgCl_2$, from about 86000 to about 103000 μM NaCl, from about 400 to about 2000 μM $NaHCO_3$, from about 250 to about 4000 μM $NaH_2PO_4$, from about 0.2 to about 2 μM $ZnSO_4$, from about 2500 to about 50000 μM glucose, from 0 to about 100 μM phenol red, and from about 23 to about 500 μM sodium pyruvate. More preferably, such a medium comprises, in final concentration, from about 900 to about 2500 μM $CaCl_2$, from about 0.1 to about 0.4 μM $Fe(NO_3)_3$, from about 4000 to about 7000 μM KCl, from 500 to about 1500 μM $MgCl_2$, from about 83000 to about 95000 μM NaCl, from about 600 to about 1200 μM $NaHCO_3$, from about 600 to about 1200 μM $NaH_2PO_4$, from about 0.4 to about 1.2 μM $ZnSO_4$, from about 15000 to about 35000 μM glucose, from about 15 to about 40 μM phenol red, and from about 150 to about 250 μM sodium pyruvate.

An especially preferred such medium comprises, in final concentration, 1800 μM $CaCl_2$, 0.2 μM $Fe(NO_3)_3$, 5360 μM KCl, 812 μM $MgCl_2$, 89000 μM NaCl, 880 μM $NaHCO_3$, 900 μM NaH$_2$PO$_4$, and 0.67 μM ZnSO$_4$, 25000 μM glucose, 23 μM phenol red, and 230 μM sodium pyruvate.

A medium of the present invention contains effective amounts of at least ten essential amino acids. In one embodiment, the medium contains, in final concentration: a) from about 250 to about 2500 μM each of L-isoleucine, L-leucine, L-threonine and L-valine; b) from about 150 to about 1500 μM L-glutamine; c) from about 120 to about 1200 μM each of L-arginine, glycine, L-phenylalanine, L-serine and L-tyrosine; d) from about 60 to about 600 μM each of L-histidine and L-methionine; e) from about 25 to about 250 μM L-tryptophan; f) from about 25 to about 250 μM L-proline; g) from about 6 to about 60 μM L-alanine; h) from about 3 to about 30 μM L-cysteine; and i) from about 1.5 to about 15 μM each of L-asparagine and L-lysine. More preferably, the medium contains, in final concentration: a) from about 500 to about 1200 μM each of L-isoleucine, L-leucine, L-threonine and L-valine; b) from about 250 to about 750 μM L-glutamine; c) from about 200 to about 600 μM each of L-arginine, glycine, L-phenylalanine, L-serine and L-tyrosine; d) from about 100 to about 300 μM each of L-histidine and L-methionine; e) from about 50 to about 125 μM L-tryptophan; f) from about 55 to about 90 μM L-proline; g) from about 15 to about 30 μM L-alanine; h) from about 7 to about 15 μM L-cysteine; and i) from about 2.5 to about 7.5 μM each of L-asparagine and L-lysine.

In a most preferred embodiment, the medium contains, in final concentration: a) 800 μM each of L-isoleucine, L-leucine, L-threonine and L-valine; b) 500 μM L-glutamine; c) 400 μM each of L-arginine, glycine, L-phenylalanine, L-serine and L-tyrosine; d) 200 μM each of L-histidine and L-methionine; e) 80 μM L-tryptophan; f) 67 μM L-proline; g) 20 μM L-alanine; h) 10 μM L-cysteine; and i) 5 μM each of L-asparagine and L-lysine.

A medium of the present invention further includes vitamins in amounts effective to sustain neural cell or tissue viability. The medium contains, in final concentration, from about 12 to about 120 μM i-inositol, from about 10 to about 100 μM niacinamide, from about 9 to about 90 μM choline chloride, from about 6 to about 60 μM pyridoxal, from about 3 to about 30 μM thiamine, from about 2.5 to about 25 μM each of folic acid and D-Ca pantothenate, from about 0.3 to about 3 μM riboflavin, and from about 0.06 to about 0.6 μM vitamin B12. More preferably, the final concentration of vitamins is from about 20 to about 60 μM i-inositol, from about 15 to about 50 μM niacinamide, from about 20 to about 40 μM choline chloride, from about 10 to about 30 μM pyridoxal, from about 5 to about 15 μM thiamine, from about 5 to about 12 μM each of folic acid and D-Ca pantothenate, from about 0.5 to about 1.5 μM riboflavin, and from about 0.1 to about 0.3 μM vitamin B12.

In an especially preferred embodiment, the medium contains, in final concentration, 40 μM i-inositol, 30 μM niacinamide, 28 μM choline chloride, 20 μM pyridoxal, 10 μM thiamine, 8 μM each of folic acid and D-Ca pantothenate, 1 μM riboflavin, and 0.2 μM vitamin B12.

II. Process of Maintaining Neural Cell Viability

A medium of the present invention has many uses, all of which are related to the ability of that medium to prolong survival of neural cells or tissues in a low CO$_2$ environment.

In one embodiment, the medium can be used to store neural cells or tissue. The cells, once obtained from any brain region, are placed in a medium and maintained under ambient CO$_2$ conditions. By way of example, tissue from the central nervous system can be placed in a medium of the present invention and stored at reduced temperature (e.g., 2° C. to 15° C.) The storage of neural cells or tissue is useful both in preparing such cells for experimental procedures and for maintaining cells prior to transplantation or implantation for therapeutic purposes. Exemplary such uses include ex vivo gene therapy, repair of damaged circuits, clonal expression and proliferating autologous or heterologous cells for transplant.

A medium of the present invention can also be used to maintain the viability of plated neural cells that are undergoing study or manipulation. Thus, for example, cells can be maintained under normal ambient conditions during electrophysiological examination. In a similar fashion, neural cells or tissue placed in a medium of the present invention can be transfected or transformed with expression vectors carrying gene inserts. Once transformed, those cells can be implanted into various regions of the brain as part of a gene therapy regimen. A medium of the present invention can also be used as a perfusate or irrigant for central nervous system tissue during central nervous system operations.

Use of a medium of the present invention has the advantage that neural cells or tissue can be studied or manipulated under normal, ambient conditions without exposing those cells or tissue to the deleterious effects of high CO$_2$ levels and changes in pH. Still further, there is no need to continuously gas a medium of the present invention. Thus, use of a medium of the present invention results in substantial time and cost savings.

When used to sustain or prolong neural cell or tissue viability, a medium of the present invention is preferably supplemented with a growth-promoting supplement that contains essential fatty acids, hormones and anti-oxidants needed for growth of the particular neural cells being cultured. Such growth-promoting media are well known in the art. By way of example, the present inventor has formulated a growth-promoting media for use with embryonic rat hippocampal cells. That medium is designated B27 and is commercially available from GIBCO/Life Technologies, Inc., Gaithersburg, Md. The growth promoting supplement, B27, contains essential fatty acids, hormones and anti-oxidants in amounts that optimize embryonic hippocampal neuron growth. The fatty acids, hormones and anti-oxidants in B27 are biotin, L-carnitine, corticosterone, ethanolamine, D(+)-galactose, reduced glutathione, linoleic acid, linolenic acid, progesterone, putrescine, retinyl acetate, selenium, triodo-1-thyronine, DL-α tocopherol, DL-α tocopherol acetate, bovine albumin, catalase, insulin, superoxide dismutase and transferrin.

The present invention also provides a composition comprising neural cells or tissue placed in a medium as set forth above. The culture can further comprise a growth-promoting supplement as set forth above.

The following Example illustrates preferred embodiments of the present invention and is not limiting of the specification and claims in any way.

EXAMPLE 1

Two basic types of experiments were conducted. In the first, rat embryonic day 18 hippocampal neurons were isolated and cultured as previously described at 160 cells/mm$^2$ in B27-supplemented Neurobasal™ (Life Technologies, Inc., Gaithersburg, Md.) on 24-well plastic substrates coated with polylysine. After 4 days in culture at 37° C. in 9% O$_2$, 5% CO$_2$, the entire medium was changed to a pre-warmed CO$_2$ independent medium supplemented with B27 as indicated. The composition of that CO$_2$ independent medium is set forth below in Table 1.

TABLE 1

| Component | Concentration in µM |
|---|---|
| inorganic salts | |
| CaCl$_2$ (anhydrous) | 1800 |
| Fe(NO$_3$)$_3$ 9H$_2$O | 0.2 |
| KCl | 5360 |
| MgCl$_2$ (anhydrous) | 812 |
| NaCl | 76000 |
| NaHCO$_3$ | 880 |
| NaH$_2$PO$_4$H$_2$O | 900 |
| ZnSO$_4$7H$_2$O | 0.67 |
| other components | |
| D-glucose | 25000 |
| phenol red | 23 |
| MOPS | 10000 |
| sodium pyruvate | 230 |
| amino acids | |
| L-alanine | 20 |
| L-arginine HCl | 400 |
| L-asparagine H$_2$O | 5 |
| L-cysteine | 10 |
| L-glutamine | 500 |
| glycine | 400 |
| L-histidine HCl H$_2$O | 200 |
| L-isoleucine | 800 |
| L-leucine | 800 |
| L-lysine HCl | 5 |
| L-methionine | 200 |
| L-phenylalanine | 400 |
| L-proline | 67 |
| L-serine | 400 |
| L-threonine | 800 |
| L-tryptophan | 80 |
| L-tyrosine | 400 |
| L-valine | 800 |
| vitamins | |
| D-Ca pantothenate | 8 |
| choline chloride | 28 |
| folic acid | 8 |
| i-inositol | 40 |
| niacinamide | 30 |
| pyridoxal HCl | 20 |
| riboflavin | 1 |
| thiamine HCl | 10 |
| vitamin B12 | 0.2 |

Culture was continued at 37° C. in a bacteriologic incubator at ambient O$_2$ and CO$_2$. The plates were placed in a Plexiglas plastic box adjacent to open dishes of water for hydration. At various times, plates were removed for counting live cells by staining with fluorescein diacetate and dead cells with propidium iodide. Survival was calculated as the number of live cells divided by the total cells (live+dead).

The data in FIG. 1 show that HEPES, bicarbonate buffered Neurobasal™ supplemented with B27 produced rapid loss of neuron viability in ambient CO$_2$, with an LD$_{50}$ of less than 6 hr. When this medium was more appropriately buffered and the bicarbonate concentration reduced, much better survival was obtained. This new formulation (See Table 1) extended the LD$_{50}$ beyond 24 hr. Slightly inferior results were obtained with a simple balanced salt solution (Hank's, Life Technologies, Inc. #14060-016) supplemented with 0.1% glucose, 1 µM sodium bicarbonate, 1 µM pyruvate, 10 µM HEPES, pH 7.3. Further improvement in viability was obtained with the use of anti-oxidants, essential fatty acids, hormones and other ingredients as in the B27 supplement. With the B27 supplement, full viability was maintained for at least 2 days in culture in ambient CO$_2$. The LD50 was extended beyond 3 days. Developed axons and dendrites showed little evidence of neurodegeneration such as retracted or beaded neurites or swollen somae. These neurons after 3 days in ambient CO$_2$ were comparable to neurons cultured in 5% C$_2$.

Comparisons of viability and sprouting were also made for ambient and 5% CO$_2$conditions after one and four days in culture. After one day, viable cells in cultures started in 5% CO$_2$ in B27-supplemented Neurobasal™ were 63±10% of those plated (mean±S.D., n=12) and 54±9% of these had neurite sprouts greater than one cell diameter. In ambient CO$_2$ and the B27-supplemented medium of Table 1, viability on day 1 was reduced to 50±7% (p<0.05) and sprouting was reduced to 22±12% (p<0.001). After 4 days, all cells were dead in the B27-supplemented medium of Table 1 in ambient CO$_2$ while normal culture in B27-supplemented Neurobasal™ in 5% CO$_2$ produced 71% viability. These data show that hippocampal neurons need a start in 5% CO$_2$ to remain healthy.

In the second type of experiment, hippocampi were dissected as usual, but placed in 2 ml of the medium of Table 1 supplemented with B27 in a 15 ml centrifuge tube (Corning, Oneonta, N.Y.). The tube was placed in a refrigerator at 8° C. At various times, the tube was removed to a laminar flow hood at room temperature. One ml of the medium was removed and saved. The hippocampus in 1 ml medium was triturated by mild suction and expulsion 10 times (or until most pieces of tissue are dispersed) through the plastic tip of a 1 ml pipettor (Gilson, Middleton, Wis.). The volume was returned to 2 ml with the original medium. After letting undispersed pieces settle for 3 min., the supernatant was transferred and centrifuged for 1 min. at 200×G. The supernatant was discarded. To loosen the pellet, the tube was agitated by hand before resuspension in 1 ml of B27-supplemented Neurobasal™ medium. After counting cells that excluded 0.2% trypan blue, cells were plated and cultured as above.

Figure 2:
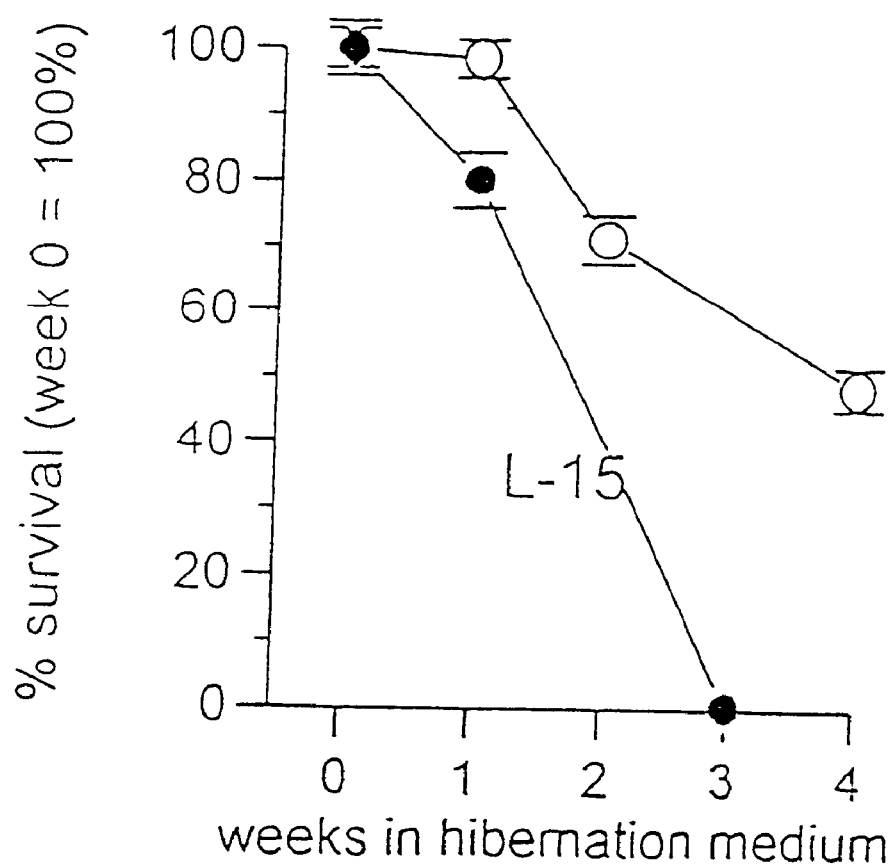
FIG. 2 shows survival of hippocampal neurons dissected from the brain and placed in either a medium of the present invention supplemented with B27(-○-) or L-15/B27(-●-) at ambient $CO_2$ levels. After storage for the indicated period at 8° C., individual cells were isolated and placed in B27-supplemented Neurobasal™ at 5% $CO_2$ for four days.

The data in FIG. 2 show that hippocampal tissue can be stored for at least one month in the refrigerator before losing half of the surviving cells, measured after 4 days in normal culture at 5% CO$_2$. These results are superior to prior studies reporting good survival after one week of storage, but little, if any, survival after 4 weeks in a low sodium, low calcium medium (Kawamoto et al, *Brain Res.*, 384:84–93, 1986). Another medium sometimes used for trituration and storage is Leibovitz's L-15, a medium with high concentrations of amino acids (Leibovitz, *Amr. J. Hyg.*, 78:173–180, 1963). The data show that the use of a medium of the present invention is superior to L-15 for refrigerated viable storage of hippocampal tissue. The yield of viable cells after 1 week of tissue hibernation in B27-supplemented medium of Table 1 was 1.3±0.3 million cells/hippocampus (mean±S.E., n=6). This is comparable to cell yields from fresh tissue.

What is claimed is:

1. A medium for maintaining neural cell or tissue viability in an environment containing less than about 0.25% CO$_2$, the medium comprising:
   a) less than about 2000 µM bicarbonate; and
   b) a buffer having a pKa of from about 6.9 to about 7.7, wherein the medium is free of ferrous sulfate, glutamate and aspartate; and
   c) from 0 to about 3000 µM CaCl$_2$, from about 0.05 to about 0.8 µM Fe(NO$_3$)$_3$, from about 2500 to about 10000 µM KCl, from 0 to about 4000 µM MgCl$_2$, from about 74000 to about 103000 µM NaCl, from about 400 to about 2000 µM NaHCO$_3$, from about 250 to about 4000 µM NaH$_2$PO$_4$, from about 0.2 to about 2 µM ZnSO$_4$, from about 2500 to about 50000 µM glucose and from about 23 to about 500 µM sodium pyruvate.

2. The medium according to claim 1 further comprising from about 0 to about 100 μM phenol red.

3. The medium according to claim 1 wherein the neural cells or tissue are of embryonic origin, and wherein the medium has an osmolality from about 210 mOsm to about 250 mOsm.

4. The medium according to claim 1 wherein the neural cells or tissue are of adult origin, and wherein the medium has an osmolality is from about 250 mOsm to about 300 mOsm.

5. The medium according to claim 4 having a bicarbonate concentration of from about 600 μM to about 1200 μM.

6. The medium according to claim 1 wherein the buffer is (3-[N-morpholino]propanesulfonic acid).

7. The medium according to claim 6 wherein (3-[N-morpholino]propanesulfonic acid) is present in a concentration of from about 5000 to about 25000 μM.

8. The medium of claim 1 comprising from about 74000 to about 81000 μM NaCl.

9. The medium of claim 1 comprising from about 900 to about 2500 μM $CaCl_2$, from about 0.1 to about 0.4 μM $Fe(NO_3)_3$ from about 4000 to about 7000 μM KCl, from 500 to about 1500 μM $MgCl_2$, from about 75000 to about 77000 μM NaCl, from about 600 to about 1200 μM $NaHCO_3$, from about 600 to about 1200 μM $NaH_2PO_4$, from about 0.4 to about 1.2 μM $ZnSO_4$, from about 15000 to about 35000 μM glucose, and from about 150 to about 250 μM sodium pyruvate.

10. The medium of claim 9 further comprising from about 15 to about 40 μM phenol red.

11. The medium of claim 10 comprising 1800 μM $CaCl_2$, 0.2 μM $Fe(NO_3)_3$, 5360 μM KCl, 812 μM $MgCl_2$, 76000 μM NaCl, 880 μM $NaHCO_3$ 900 μM $NaH_2PO_4$, 0.67 μM $ZnSO_4$, 25000 μM glucose, 230 μM sodium pyruvate and 23 μM phenol red.

12. The medium according to claim 1 comprising a) from about 250 to about 2500 μM each of L-isoleucine, L-leucine, L-threonine and L-valine; b) from about 150 to about 1500 μM L-glutamine; c) from about 120 to about 1200 μM each of L-arginine, glycine, L-phenylalanine, L-serine and L-tyrosine; d) from about 60 to about 600 μM each of L-histidine and L-methionine; e) from about 25 to about 250 μM L-tryptophan; f) from about 25 to about 250 μM L-proline; g) from about 6 to about 60 μM L-alanine; h) from about 3 to about 30 μM L-cysteine; and i) from about 1.5 to about 15 μM each of L-asparagine and L-lysine.

13. The medium of claim 12 comprising a) from about 500 to about 1200 μM each of L-isoleucine, L-leucine, L-threonine and L-valine; b) from about 250 to about 750 μM L-glutamine; c) from about 200 to about 600 μM each of L-arginine, glycine, L-phenylalanine, L-serine and L-tyrosine; d) from about 100 to about 300 μM each of L-histidine and L-methionine; e) from about 50 to about 125 μM L-tryptophan; f) from about 55 to about 90 μM L-proline; g) from about 15 to about 30 μM L-alanine; h) from about 7 to about 15 μM L-cysteine; and i) from about 2.5 to about 7.5 μM each of L-asparagine and L-lysine.

14. The medium of claim 13 comprising a) 800 μM each of L-isoleucine, L-leucine, L-threonine and L-valine; b) 500 μM L-glutamine; c) 400 μM each of L-arginine, glycine, L-phenylalanine, L-serine and L-tyrosine; d) 200 μM each of L-histidine and L-methionine; e) 80 μM L-tryptophan; f) 67 μM L-proline; g) 20 μM L-alanine; h) 10 μM L-cysteine; and i) 5 μM each of L-asparagine and L-lysine.

15. The medium according to claim 1 comprising from about 12 to about 120 μM i-inositol, from about 10 to about 100 μM niacinamide, from about 9 to about 90 μM choline chloride, from about 6 to about 60 μM pyridoxal, from about 3 to about 30 μM thiamine, from about 2.5 to about 25 μM each of folic acid and D-Ca pantothenate, from about 0.3 to about 3 μM riboflavin, and from about 0.06 to about 0.6 μM vitamin B12.

16. The medium of claim 15 comprising from about 20 to about 60 μM i-inositol, from about 15 to about 50 μM niacinamide, from about 20 to about 40 μM choline chloride, from about 10 to about 30 μM pyridoxal, from about 5 to about 15 μM thiamine, from about 5 to about 12 μM each of folic acid and D-Ca pantothenate, from about 0.5 to about 1.5 μM riboflavin, and from about 0.1 to about 0.3 μM vitamin B12.

17. The medium of claim 16 comprising 40 μM i-inositol, 30 μM niacinamide, 28 μM choline chloride, 20 μM pyridoxal, 10 μM thiamine, 8 μM each of folic acid and D-Ca pantothenate, 1 μM riboflavin, and 0.2 μM vitamin B12.

18. A composition comprising neural cells or tissue placed in the medium of claim 1.

19. The composition of claim 18 that is supplemented with a serum-free growth promoting supplement that comprises effective amounts of hormones, essential fatty acids and anti-oxidants.

20. The composition of claim 19 wherein the growth promoting supplement contains biotin, L-carnitine, corticosterone, ethanolamine, D(+)-galactose, reduced glutathione, linoleic acid, linolenic acid, progesterone, putrescine, retinyl acetate, selenium, triodo-1-thyronine, DL-α tocopherol, DL-α tocopherol acetate, bovine albumin, catalase, insulin, superoxide dismutase and transferrin.

21. A holding mixture comprising neural cells or tissue in the medium of claim 1.

22. A process of extending neural cell or tissue viability in an atmosphere having a carbon dioxide concentration of less than about 0.25% comprising placing the neural cells or tissue in the medium of claim 1 and maintaining the cells or tissue in the atmosphere.

23. The process of claim 22 wherein the medium is supplemented with a serum-free growth promoting supplement that comprises effective amounts of hormones, essential fatty acids and anti-oxidants.

24. The process of claim 23 wherein the growth-promoting supplement contains biotin, L-carnitine, corticosterone, ethanolamine, D(+)-galactose, reduced glutathione, linoleic acid, linolenic acid, progesterone, putrescine, retinyl acetate, selenium, triodo-1-thyronine, DL-α tocopherol, DL-α tocopherol acetate, bovine albumin, catalase, insulin, superoxide dismutase and transferrin.

* * * * *

UNITED STATES PATENT AND TRADEMARK OFFICE
CERTIFICATE OF CORRECTION

PATENT NO. : 6,180,404 B1
DATED : January 30, 2001
INVENTOR(S) : Gregory J. Brewer et al.

Page 1 of 1

It is certified that error appears in the above-identified patent and that said Letters Patent is hereby corrected as shown below:

Column 2,
Line 28, please delete "amo unts" and insert -- amount --
Line 31, please delete "L-isoleuoine" and insert -- L-isoleucine --

Column 4,
Line 46, please delete "osmolalilty is is from" and insert -- osmolality is from --

Column 9,
Line 9, please delete "osmolality is from" and insert -- osmolality from --

Signed and Sealed this

Sixteenth Day of October, 2001

Attest:

Nicholas P. Godici

NICHOLAS P. GODICI
Attesting Officer   Acting Director of the United States Patent and Trademark Office